United States Patent [19]

Kaluza et al.

[11] Patent Number: 5,183,747
[45] Date of Patent: Feb. 2, 1993

[54] TYPE II RESTRICTION ENDONUCLEASE SSP4800I

[75] Inventors: Klaus Kaluza, Bad Heilbrunn; Bruno Frey, Penzberg; Michael Jarsch, Bad Heilbrunn, all of Fed. Rep. of Germany

[73] Assignee: Boehringer Mannheim GmbH, Mannheim, Fed. Rep. of Germany

[21] Appl. No.: 777,759

[22] Filed: Oct. 10, 1991

[30] Foreign Application Priority Data

Oct. 11, 1990 [DE] Fed. Rep. of Germany ....... 4032213

[51] Int. Cl.⁵ ........................ C12P 19/34; C12N 9/22
[52] U.S. Cl. ................................. 435/91; 435/199
[58] Field of Search ................................. 435/199, 91

[56] References Cited

PUBLICATIONS

Kessler, C., et al, (1990) Gene 92, 1-248.

Roberts, R. J., et al. (1992) Nuc. Acids Res 20 (Suppl), 2162-2180.

*Primary Examiner*—Charles L. Patterson, Jr.
*Attorney, Agent, or Firm*—Felfe & Lynch

[57] ABSTRACT

The new type II restriction endonuclease Ssp4800I has the following recognition sequence:

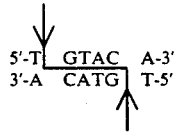

and preferably cleaves at the cleavage site defined by the arrows. It is preferably obtainable from microorganisms of the genus Streptomyces.

10 Claims, No Drawings

TYPE II RESTRICTION ENDONUCLEASE SSP4800I

The invention concerns the new type II restriction endonuclease Ssp4800I, a process for its isolation and its use.

Type II restriction endonucleases are endodeoxyribonucleases which are able to recognize and cleave particular DNA sequences. In this process one phosphodiester bridge in each polynucleotide strand of the target sequence are hydrolyzed. Type II restriction endonucleases are thus of value for the analysis of DNA molecules. Although type II restriction endonucleases are known which are specific for numerous DNA sequences, there is still a need to for further type II restriction endonucleases which are specific for DNA sequences and which up to now have not been recognized by any of the known restriction endonucleases. The object of the invention is therefore to provide a new restriction endonuclease which is able to specifically recognize and cleave a sequence which has not been recognized up to know by any such enzyme.

This object is achieved according to the present invention by a type II restriction endonuclease having the recognition sequence

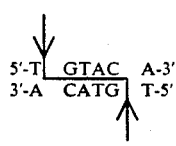

and the cleavage site defined by the arrows.

The new restriction endonuclease according to the present invention, which is denoted Ssp4800I hereafter, has a temperature optimum at 50° C. The enzyme has good activity between pH 7.5 and pH 8.5 in 10 mmol/l Tris/HCl buffer with 1.0 mmol/l 2-mercapto-ethanol, 5 mmol/l MgCl$_2$ and 100 mmol/l NaCl. The pH optimum is at pH 8.0.

The recognition sequence can be confirmed by the complete digestion of the DNAS of the viruses SV40 and adeno 2, of the phages lambda, phiX174, the phage derivative M13mp7 and of the plasmids pBR322 and pBR328. These DNA molecules are treated with Ssp4800I.

Table 1 shows a comparison of the cleavage site specificity observed experimentally with a cleavage site specificity determined by computer for an enzyme which recognizes the following sequence:

5'-TGTACA-3'

TABLE 1

| DNA | Number of cleavage sites determined experimentally | Number of cleavage sites determined by computer analysis | Fragment lengths (base pairs) determined experimentally | | Fragment lengths (base pairs) determined by computer analysis | | Cleavage positions determined by computer analysis (at base pair) | | |
|---|---|---|---|---|---|---|---|---|---|
| SV40 | 2 | 2 | 3800 | 1400 | 3832 | 1411 | 3579 | 4990 | |
| M13mp7 | 1 | 1 | 7200 | | 7238 | | 1025 | | |
| PhiX174 | 0 | 0 | 0 | | 0 | | 0 | | |
| pBR322 | 0 | 0 | 0 | | 0 | | 0 | | |
| pBR328 | 0 | 0 | 0 | | 0 | | 0 | | |
| Lambda | 5 | 5 | 16000 | 13500 | 16002 | 13537 | 5224 | 6146 | 15859 |
|  |  |  | 9700 | 5200 | 9713 | 5224 | 29396 | 32500 |  |
|  |  |  | 3100 | 922 | 3104 | 922 |  |  |  |
| Ad2 | 5 | 5 | 12000 | 6800 | 11614 | 6811 | 2247 | 8120 | 19734 |
|  |  |  | 6700 | 5900 | 6682 | 5873 | 22444 | 29126 |  |
|  |  |  | 2700 | 2300 | 2710 | 2247 |  |  |  |

The cleavage position within the recognition sequence of the enzyme can be determined with a M13 derivative having this recognition sequence at a distance of ca. 30-200 bases from the binding site of the universal sequencing primer (Messing, J. et al., (1981) Nulc. Acids Res. 9, 309-321). At first sequence reactions according to the dideoxy chain-termination method (Sanger, F. et al., (1977) Proc. Natl. Acad. Sci. USA 74, 560-564, Messing, J. et al., (1981) Nucl. Acids Res. 9, 309-321) are carried out on the single-stranded stranded DNA of the M13 derivative with the universal sequencing primer.

Parallel to this, the sequencing primer is radioactively labelled at the 5' end with T4-polynucleotide kinase and [$^{32}$P]ATP. After hybridization of this 5' end-labelled sequencing primer to the single-stranded M13 DNA, a partially double-stranded DNA is prepared in a "filling up" reaction with DNA-polymerase I, (Klenow enzyme) and a deoxynucleotide triphosphate mixture of dATP, dCTP, dGTP and dTTP. This DNA, the newly synthesized strand of which is radioactively labelled at the 5' end, is now cleaved with the restriction endonuclease Ssp4800I. Half of the cleavage preparation is also treated with T4-DNA polymerase in the presence of a mixture of all four deoxynucleotide triphosphates in order to obtain blunt DNA ends.

The analysis of the reaction products is carried out by electrophoresis on sequencing gels (8 mol/l urea, 5% polyacrylamide) and subsequent autoradiography. The results are interpreted according to Brown, N.L. and Smith, M. (Methods in Enzymology 65 (1980) 391-401). The position of the cleavage site is determined by a comparison of the distances of migration of the radioactively-labelled fragments with the sequencing ladder. The samples which were additionally treated with T4-DNA polymerase show a 4bp longer distance of migration of the bands in comparison with the sample which was only cleaved with Ssp4800I. This therefore shows that Ssp4800I produces a 5' DNA end which protrudes by 4bp. The cleavage of Ssp4800I has therefore the following specificity within the recognition sequence:

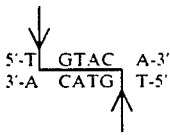

The number of cleavage sites determined experimentally is identical to the number of cleavage sites obtained by computer analysis with the different DNA's (Table I) for the sequence

5'-TGTACA-3'

In addition these data were also compared with the tables in Gene 10 (1980) 357-370.

Ssp4800I is preferably isolated by culturing microorganisms of the genus Streptomyces and isolating the enzyme from the cells. The strain Streptomyces spec. BMTU 4800 (DSM 6181) is particularly preferred.

The microorganism Streptomyces spec. BMTU 4800 is deposited at the German Collection of Microorganisms (DSM), Mascheroder Weg 16, 3300 Braunschweig, GFR and has the deposit number DSM 6181.

The usual biochemical methods of purification can be used for the isolation of the enzyme in which the presence of the enzyme in the respective fractions obtained can be easily tested on the basis of the cleavage of its recognition sequence. Lambda DNA is, for example suitable as the substrate. The DNA fragments obtained are separated electrophoretically on agarose gels in buffer systems usually used for the fragment separation in the presence of ethidium bromide.

The microorganisms used for the isolation of the enzyme grow aerobically in M111 medium (10 g/l yeast extract, 10 g/l malt extract). The optimal conditions for growth are pH 6.5-7.5 at 26° C. The doubling time is about 2.5 hours.

The enzyme is isolated and purified by the usual chemical and mechanical methods such as by high pressure dispersion, ultrasound or enzymatic lysis. In a preferred embodiment of the process according to the present invention the cells are lysed by means of a French press. Further purification of the supernatant is preferably carried out by means of affinity chromatography and ion-exchange chromatography. Heparin-Sepharose CL-6B (Pharmacia) is, for example, suitable as the material for the affinity chromatography. A suitable cation-exchanger is, for example, phosphocellulose (Whatman).

The product available under the name DEAE Sephacel (Pharmacia) is suitable as the anion-exchanger; other chromatographic materials which are known to one skilled in the art are also suitable. The following examples elucidate the invention further

EXAMPLE 1

The microorganism Streptomyces spec. BMTU 4800 (DSM 6181) is cultured for 10-12 hours at 26° C. and harvested at the end of the late logarithmic phase. M111 medium is used as the culture medium.

The cell paste (30 g wet weight) is resuspended in 2.4 volumes buffer A (40 mmol/l Tris-HCl, pH 8.0, 0.1 mmol/l EDTA, 7 mmol/l 2-mercaptoethanol) which contains protease inhibitors. Subsequently the cells are lysed by passing them twice through a French press at 23000 lb/inch$^2$ and the precipitate is separated off. NH$_4$Cl (final concentration 0.3 mol/l) is added to the supernatant. The nucleic acids are removed by a Polymin precipitation. Subsequently the centrifuged supernatant is treated with 60 % (w/v) ammonium sulphate and the precipitate is fractionated on a heparin-Sepharose column. A gradient of 0-1mol/l NaCl is used for the elution. Ssp4800I is found in the fractions between 0.5 and 0.7 mol/l NaCl. The active fractions are equilibrated against buffer B (40 mmol/l Tris-HCl, pH 8.0; 0.1 mmol/l EDTA; 7 mmol/l 2-mercaptoethanol; 10% (v/v) glycerol) and fractionated on a DEAE fast flow column. A gradient of 0-0.5 mol/l NaCl is used for the elution. The active fractions are dialyzed against buffer B.

Subsequently they are loaded onto a phosphocellulose column which has been equilibrated with buffer B. A gradient of 0-1 mol/l NaCl in buffer B is used for the elution.

The active fractions are pooled and dialyzed against storage buffer (20 mmol/l Tris-HCl, pH 8.0, 10 mmol/l 2-mercaptoethanol, 100 mmol/l NaCl, 0.1 mmol/l EDTA and 50% (v/v) glycerol).

EXAMPLE 2

Determination of the activity

Definition of the enzyme units: 1 U Ssp4800I cleaves 1 μg lambda DNA within 1 hour at 50° C. in 25 μl final volume. 17.9 μl water and 3.6 μl lambda DNA (optical density: 5.6 OD/ml) as well as 1 μl Ssp48001 solution (1 U/μl) are added to a mixture of 2.5 μl incubation buffer (100 mmol/l Tris-HCl, pH 8.0, 50° C., 50 mmol/l magnesium chloride, 1 mmol/l NaCl, and 10 mmol/l 2-mercapto-ethanol). The solution is incubated for 1 hour at 37° C., cooled on ice and 5 μl of a stopping reagent consisting of 7 mmol/l urea, 20% (w/v) sucrose, 60 mmol/l EDTA and 0.01% (w/v) bromophenol blue is added. Subsequently a separation is carried out by electrophoresis in 1 % agarose gels for 3-4 hours at 100 V. The bands obtained are identified by comparison with a DNA length standard.

We claim:

1. Type II restriction endonuclease having the recognition sequence

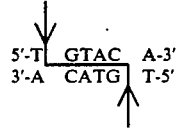

and the cleavage site indicated by the arrows.

2. Type II restriction endonuclease as claimed in claim 1, obtained from microorganisms of the genus Streptomyces.

3. Type II restriction endonuclease as claimed in claim 1, obtained from Streptomyces Sp. BMTU 4800 (DSM 6181).

4. Type II restriction endonuclease as claimed in claim 1, characterized by a temperature optimum of 50° C. and a pH optimum of 8.0.

5. Process for the isolation of a type-II restriction endonuclease having the recognition sequence

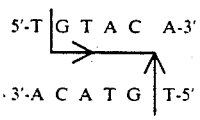

and the cleavage site indicated by the arrows comprising culturing a microorganism of the genus Streptomyces to produce said restriction endonuclease and isolating said restriction endonuclease therefrom.

6. Process as claimed in claim 5, wherein said Streptomyces is Streptomyces Sp. BMTU 4800 (DSM 6181).

7. Process as claimed in claim 5 comprising lysing cells of said microorganism to form a supernatant and isolating said endonuclease from said supernatant.

8. Process as claimed in claim 7, further comprising subjecting said supernatant to affinity chromatography, anion exchange chromatography, and cation-exchange chromatography to isolate said endonuclease from said supernatant.

9. Process as claimed in claim 8, comprising using carrier-bound heparin for affinity chromatography.

10. Method for obtaining a DNA sequence having terminal nucleotide sequence:

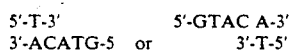

comprising contacting a sample of DNA with the restriction endonuclease of claim 1 and separating cleavage products produce thereby.

* * * * *